Feb. 5, 1957 E. H. DOERR Plant Pat. 1,560
RED GLADIOLUS PLANT
Filed Feb. 2, 1956
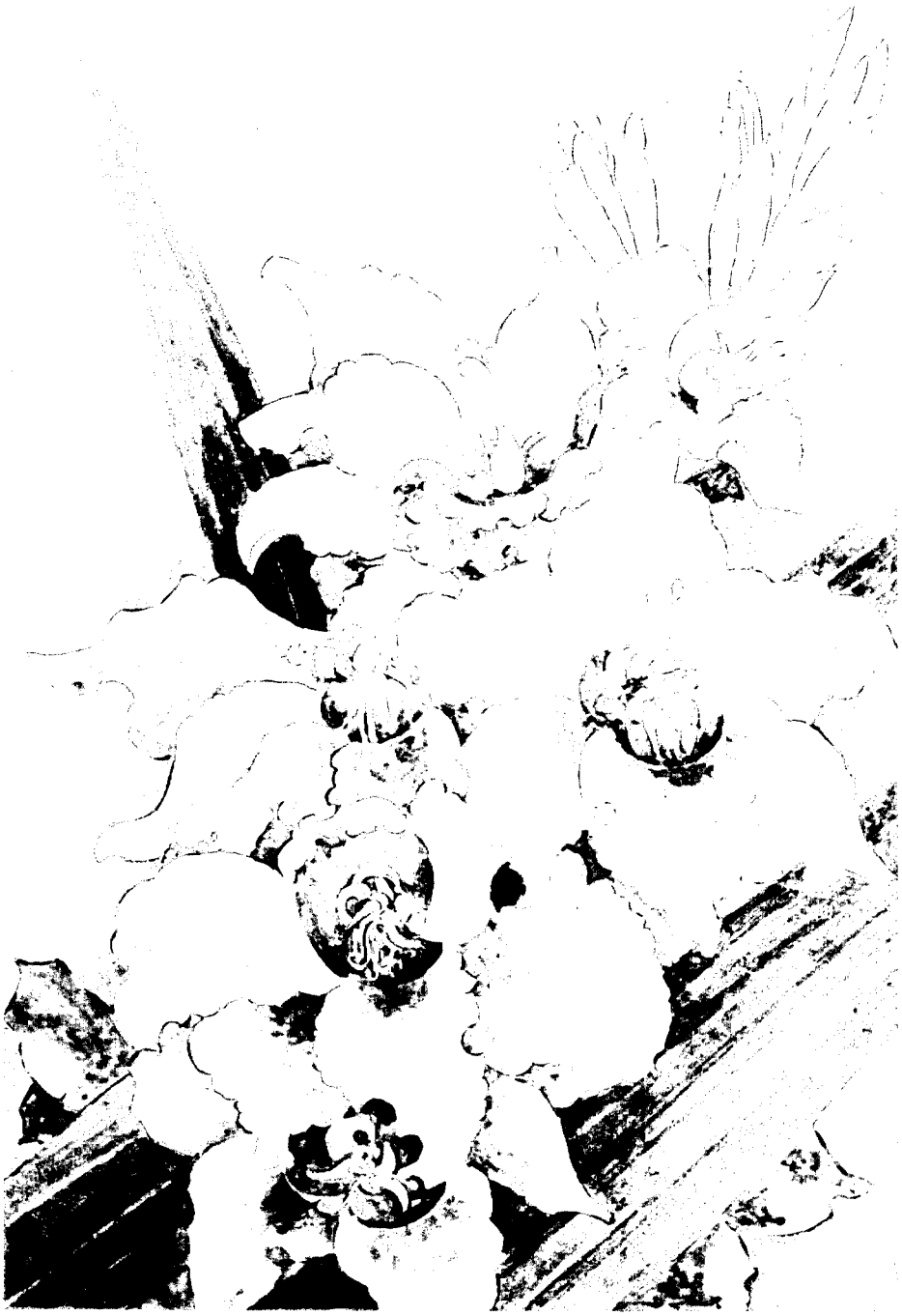
WITNESS
Addison J. Avery
INVENTOR
ERVIN H. DOERR
by Rummler, Rummler & Snow
ATTYS.

United States Patent Office

Plant Pat. 1,560
Patented Feb. 5, 1957

1,560

RED GLADIOLUS PLANT

Ervin H. Doerr, New Ulm, Minn.

Application February 2, 1956, Serial No. 563,158

1 Claim. (Cl. 47—60)

My present invention relates to a new and improved variety of red gladiolus plant which originated as a seedling, identified by me as #1105-1, at my gardens in New Ulm, Minnesota, from a cross between the variety "King David" (not patented), as the seed parent and an unnamed double seedling as the pollen parent.

This new variety is a result of breeding effort carried on by me since 1940 and my asexual reproduction of this new variety for several years, from cormels grown into blooming size bulbs, at New Ulm, Minnesota, has shown its desired qualities and characteristics to be permanently fixed.

The primary object in carrying out this invention was to establish the distinctive, deep, dark red color of the flowers. This variety is essentially like its parent "King David" in its form of floret and growth of plant.

The accompanying illustration shows in full color a cluster of flowers and leaves.

In general plant structure, this new variety is similar to the gladioli family, leaves growing on the upper portion of a stem, flowers more or less tubular, the tube usually funnel-shaped, enlarging upward, with three stamens inserted in the tube. The leaves are several ribbed, varying from linear to sword-shaped.

This new variety is distinctly and outstandingly different from the parent "King David" especially with respect to the shiny, velvety dark red coloring of its large blooms, forming magnificent spikes such as no other gladiolus has. Its stamens also carry petaloids of a dark red color which fill the center of the florets and give them a double appearance. The pistils are white-tipped contrasting vividly with the dark red of the flower.

The plant has a vigorous growth with abundant foliage and grows to a heighth of about three feet. The plant blooms once, late in the season; and the florets are large, opening to about 4½ inches, with 6 petals of more or less standard form. The flowers are not affected by wet or hot weather and have very good lasting qualities both on the plant and as a cut flower.

The following is a detailed description of my new gladiolus variety:

Parentage: Seedling.
*Seed parent.*—"King David."
*Pollen parent.*—An unnamed double seedling.

Flower:
*Blooms.*—Once—late.
*Size.*—Large—4½ inches.
*Petalage.*—6 for each floret.
*Form.*—Standard.
*Petaloids.*—Yes.
*Color.*—Outer petals, dark red; inner petals, dark red; base, darker red.
*Petal texture.*—Leathery.
*Appearance.*—Shiny and velvety.
*Affected by wet or hot weather.*—No.
*Persistence (hang on and dry).*—Good.
*Lasting qualities.*—On plant and as cut flower—very good.
Bud: Average size and form.
Plant:
*Height.*—3 feet.
*Growth.*—Vigorous.
*Foliage.*—Abundant.
*Corms.*—Yes.
Genital organs:
*Stamens.*—Anthers carry petaloids. Length—average.
*Number.*—3.
*Color.*—Red. Arrangement: normal.
*Pollen.*—Color, red.
*Pistil.*—One, having 3 white stigmas branching from a long style.
*Ovaries.*—Abnormal.

The color designations according to "A Dictionary of Color by Maerz and Paul" are as follows:

| | Plate | Letter | No. |
|---|---|---|---|
| Lightest red base of three top major petals | 2 | K | 10 |
| to darkest red top of top major petals | 3 | L | 12 |
| Lightest red of three lower minor petals | 3 | L | 12 |
| dark area at throat on three lower major petals | 4 | L | 12 |
| small long narrow petaloids | 4 | L | 12 |
| Pistil—One (three-branched at tip) | 1 | K | 8 |
| stigma tips—white | 1 | A | 1 |
| Stamens—3 (white bird-bill-like formation) | 1 | A | 1 |
| on end of red stem | 1 | L | 7 |
| Leaf—Green: | | | |
| from | 21 | L | 7 |
| to | 22 | L | 8 |

The brilliant pure red coloring of this new variety together with its double-petal appearance, its vigorous growth, the good keeping qualities of its blooms both on the plant and as cut flowers and its late blooming habit combine to make a spectacular commercial product.

Having thus disclosed my invention, I claim:

A new and distinct variety of gladiolus plant, substantially as herein shown and described, characterized particularly by the pure all-over red coloring of the blooms, its white stamens and white tipped pistils, the narrow red petaloids which give a double appearance to the blooms, the late blooming habit of the plant, and its vigorous growth.

No references cited.